United States Patent [19]
Manami et al.

[11] Patent Number: 5,091,564
[45] Date of Patent: Feb. 25, 1992

[54] PROCESS FOR PREPARING DIPHENYL SULFONETETRACARBOXYLIC ACID

[75] Inventors: Hiroshi Manami, Jyoyo; Mikio Nakazawa, Uji; Shigeo Miki, Hirakata; Akihiro Nishiuchi, Jyoyo, all of Japan

[73] Assignee: New Japan Chemical Co., Ltd., Kyoto, Japan

[21] Appl. No.: 585,698

[22] Filed: Sep. 20, 1990

[30] Foreign Application Priority Data

Sep. 27, 1989 [JP] Japan .................. 1-251598

[51] Int. Cl.$^5$ .................................... C07C 51/265
[52] U.S. Cl. ........................ 562/416; 562/417; 562/427
[58] Field of Search ............... 562/416, 417, 427

[56] References Cited

U.S. PATENT DOCUMENTS

| | | | |
|---|---|---|---|
| 3,139,452 | 6/1964 | Hay | 562/416 |
| 3,504,022 | 3/1970 | Bresson | 562/416 |
| 4,827,025 | 5/1989 | Shiraki et al. | 562/414 |

Primary Examiner—Jose G. Dees
Assistant Examiner—Vera C. Clarke
Attorney, Agent, or Firm—Larson and Taylor

[57] ABSTRACT

Disclosed is a process for preparing a diphenyl sulfonetetracarboxylic acid, the process comprising oxidizing a tetramethyldiphenyl sulfone with oxygen or an oxygen-containing gas in an aliphatic monocarboxylic acid having 2 to 10 carbon atoms in the presence of a catalyst consisting essentially of a cobalt component, a manganese component and a bromine compound wherein the weight ratio of manganese metal to cobalt metal is in the range of approximately 0.01 to 0.5.

22 Claims, No Drawings

PROCESS FOR PREPARING DIPHENYL SULFONETETRACARBOXYLIC ACID

BACKGROUND OF THE INVENTION

1. Field of the Invention

The present invention relates to a process for preparing a diphenyl sulfonetetracarboxylic acid.

Diphenyl sulfonetetracarboxylic acids have wide applications, for example, as materials for preparation of polyimide, polyamide-imide, polyester-imide or like resins, curing agents for epoxy resin, plasticizers, lubricants, agricultural chemicals, dyes or the like. An all-aromatic polyimide prepared by reaction of a dianhydride of said tetracarboxylic acid with an aromatic diamine is attracting attention in the fields of electrical and electronic technologies, aircraft, spacecraft, automobiles, etc. because of its high heat resistance and its excellent mechanical and electrical characteristics.

2. Prior Art

It is known to produce 3,3',4,4'-diphenyl sulfonetetracarboxylic acid by oxidizing 3,3', 4,4'-tetramethyldiphenyl sulfone with a molecular oxygen ($O_2$). For example, an oxidation method (method 1) is known which is conducted in a solvent mixture of acetic acid and haloacetic acid such as trifluoroacetic acid, trichloroacetic acid or the like in the presence of a cobalt-manganese-bromine compound type catalyst wherein the cobalt metal and manganese metal are used in equimolar ratio [Khim. Prom. (Moscow), (5), 393 (1974)]. This method requires expensive and highly corrosive trifluoroacetic acid or trichloroacetic acid as the solvent component, hence commercially disadvantageous.

Another known method (method 2) employs as catalyst a bromine compound and an equimolar mixture of at least three IV-group metals of the periodic table, such as cobalt-manganese-chromium or cobalt-manganese-nickel and uses acetic acid as the solvent (U.S.S.R. Patent No. 422,730). This method gives a reaction product of undesirable coloration with a low purity in a low yield because the reaction is not completed.

It should be noted that diphenyl sulfone-tetracarboxylic acids to be used for the preparation of polyimide, especially pale-colored polyimide resin, must have a high purity and a low degree of coloration. The product resulting from such incomplete reaction as above contains impurities such as diphenyl sulfonetricarboxylic acid and diphenyl sulfonedicarboxylic acid and structurally unidentified various colored materials. Since these impurities are close in properties to the desired diphenyl sulfonetetracarboxylic acid, great difficulty is encountered in purifying the diphenyl sulfoneteracarboxylic acid by removal of the impurities. Consequently it is essential that the oxidation reaction give a high-purity, pale-colored product in order to satisfy the requirements necessary for use as a starting material for preparing polyimide. The above-mentioned method 2 remains to be improved in this respect.

SUMMARY OF THE INVENTION

An object of the present invention is to provide a commercially advantageous process for preparing a high-purity, pale-colored diphenyl sulfonetetracarboxylic acid in high yields.

According to the invention, there is provided a process for preparing a diphenyl sulfonetetracarboxylic acid, the process comprising oxidizing a tetramethyldiphenyl sulfone with oxygen or an oxygen-containing gas in an aliphatic monocarboxylic acid having 2 to 10 carbon atoms in the presence of a catalyst consisting essentially of a cobalt component, a manganese component and a bromine compound wherein the weight ratio of the manganese metal to the cobalt metal is in the range of approximately 0.01 to 0.5.

We conducted extensive research giving our attention to the composition of a catalyst which is used in a process for preparing a diphenyl sulfonetetracarboxylic acid comprising the step of oxidizing a tetramethyldiphenyl sulfone with a molecular oxygen in a solvent such as acetic acid or like aliphatic monocarboxylic acid in the presence of a catalyst. Our finding was that when a cobalt-manganese-bromine compound combination is used as a catalyst, the weight ratio of manganese metal to cobalt metal (hereinafter referred to as "Mn/Co ratio") significantly affects the oxidation reaction.

That is to say, the Mn/Co ratio employed in the conventional reaction, specifically the ratio of the order of about 1, results in failure to achieve a satisfactory degree of conversion so that the obtained crude reaction product has a low purity and high degree of coloration. On the other hand, when the above-specified range of Mn/Co ratio is selected, a high degree of conversion is attained, giving a high-purity, properly pale-colored diphenyl sulfonetetracarboxylic acid. Furthermore, with the foregoing specific range of Mn/Co ratio, the reaction can easily proceed without undesired interruption or great variation of reaction rate.

The present invention has been accomplished based on these novel findings.

DETAILED DESCRIPTION OF THE INVENTION

The catalyst of the invention is constituted by a cobalt component, a manganese component and a bromine compound.

The cobalt component and manganese component to be added to the reaction system to form a catalyst may be in any of forms including metal form (metal cobalt or metal manganese), oxides, hydroxides, salts, complexes and the like. Of the salts, preferred are salts of an organic acid such as acetic acid, propionic acid, capric acid or naphthenic acid or salts of an inorganic acid such as hydrogen bromide or hydrogen chloride.

Useful bromine compounds to be added to the reaction system are those having at least one bromine atom in the molecule, and can be any of bromine molecule, hydrogen bromide, bromic acid ($HBrO_3$), hypobromous acid ($HBrO$), bromides such as ammonium bromide and metal bromides, bromates, hypobromites and organic bromine compounds. Preferred examples of the bromine compounds for use herein are hydrogen bromide, ammonium bromide, alkali metal bromides such as sodium bromide or potassium bromide, alkaline earth metal bromides such as calcium bromide or magnesium bromide, cobalt bromide, manganese bromide, cerium bromide, brominated lower hydrocarbons such as tetrabromoethane, tribromoethane, etc.

When a bromine-containing cobalt or manganese compound, salt or complex, such as cobalt bromide or manganese bromide, is used as a bromine compound, it also acts as the cobalt component or manganese component. The cobalt component, manganese component and bromine compound may be added to the reaction system separately or in the form of a mixture or in the form of a compound.

Preferred examples of the catalyst for use herein are combinations of cobalt bromide-manganese bromide; cobalt bromide-manganese acetate; cobalt acetate-manganese acetate-hydrogen bromide; cobalt acetate-manganese acetate-ammonium bromide; cobalt bromide-manganese naphthenate; cobalt naphthenate-manganese naphthenate-hydrogen bromide; cobalt acetate-manganese naphthenate-tetrabromoethane; cobalt acetate-manganese acetate-sodium bromide; cobalt acetate-manganese bromide-cerium bromide; etc.

A suitable amount of the cobalt component to be used is about 0.01 to about 20 g, preferably about 0.01 to about 10 g (calculated as cobalt metal), per liter of the combined amount of the components (such as catalyst, starting material and solvent) present in the liquid phase of the reaction system. The term "g/l" used throughout the specification and the appended claims means grams per liter of the components present in the liquid phase of the reaction system. If less than 0.01 g/l of the cobalt component is used, it is often difficult to obtain a satisfactory reaction rate. On the other hand, if the amount of the cobalt component exceeds 20 g/l, an increased cost of catalyst is incurred and the reaction product tends to become difficult to purify.

A suitable amount of the manganese component to be used is about 0.01 to about 0.5, preferably about 0.01 to about 0.3, in a weight ratio of the manganese component to the cobalt component, calculated as metal. If the manganese component is used in the Mn/Co ratio of less than 0.01, the reaction tends to be incomplete, giving a reaction product which has low degree of coloration but has a low purity in a low yield, and the reaction rate tends to decrease pronouncedly during the reaction, making the completion of reaction difficult. If the Mn/Co ratio exceeds 0.5, the reaction also tends to be incomplete, giving in a low yield a reaction product which has a low purity and is highly colored, entailing difficulty in decoloring and purifying the reaction product. If the Mn/Co ratio is about 0.01 to about 0.5, the reaction stably proceeds and is completed without marked reduction of reaction rate, giving the desired product with low degree of coloration and high purity of at least about 95% in a yield of at least about 97%.

A suitable amount of the bromine compound to be used is about 0.05 to about 100 g/l, preferably about 0.05 to about 50 g/l, calculated as bromine atom. The use of less than 0.05 g/l of bromine compound makes it impossible to attain the desired reaction rate, whereas the use of more than 100 g/l thereof leads to contamination of desired reaction product due to the bromine and to an increase in the cost of catalyst, hence undesirable.

The tetramethyldiphenyl sulfones to be used as the starting material in the present invention are compounds wherein four methyl groups are directly bonded to the benzene nuclei of diphenyl sulfone. The four methyl groups may be present at any positions of the benzene nuclei. Examples of such compounds are:

3,3',4,4',-tetramethyldiphenyl sulfone,
2,3,3',4'-tetramethyldiphenyl sulfone,
2,2',3,3'-tetramethyldiphenyl sulfone,
2,2',4,4',-tetramethyldiphehyl sulfone,
2,2',3,4'-tetramethyldiphenyl sulfone,
2,2',5,5'-tetramethyldiphenyl sulfone,
2,2',6,6'-tetramethyldiphenyl sulfone,
3,3',5,5'-tetramethyldiphenyl sulfone, etc.

These sulfones are usable singly or at least two of them can be used in mixture.

The amount of the tetramethyldiphenyl sulfone to be used is selectable from a wide range, and is usually about 35 to about 950 g/l, preferably about 50 to about 500 g/l.

An aliphatic carboxylic acid having 2 to 10 carbon atoms is used as the solvent in the reaction of the invention. It is suitable to use a lower saturated aliphatic carboxylic acid, preferably acetic acid, which is relatively stable in oxidation and easy to separate from the reaction product. The amount of the solvent to be used is variable depending on the kind of starting material and other reaction conditions, and is usually in the range of about 50 to about 920 g/l, preferably about 475 to about 910 g/l.

While the molecular oxygen serving as the oxidizing agent includes pure oxygen and industrial discharged gas, air is commercially optimal.

The reaction temperature is about 100° to about 250° C., preferably about 150° to about 210° C. A reaction temperature of less than 100° C. reduces the reaction rate, whereas a reaction temperature exceeding 250° C. initiates the decomposition of solvent or reaction product to carbon dioxide, hence undesirable.

As to the reaction pressure, the total reaction pressure is preferably in the range of about 1 to about 50 kg/cm$^2$G, more preferably about 3 to about 30 kg/cm$^2$G, and the partial pressure exerted by oxygen is preferably in the range of about 0.01 to about 8.0 kg/cm$^2$, more preferably about 0.01 to about 6.0 kg/cm$^2$. Usually oxygen gas or oxygen-containing gas such as air is introduced into the liquid phase of the reaction system. Thus, while the oxygen or oxygen-containing gas is passing through the liquid phase, often the oxygen may be totally consumed, and therefore the partial pressure of oxygen may become zero. Thus, in the reaction of this invention, the partial presuure of oxygen is preferably adjusted to about 8.0 kg/cm$^2$ or lower, more preferably about 6.0 kg/cm$^2$ or lower.

The process of the invention is usually carried out as follows.

The starting material, the catalyst and the solvent to be used in the invention are charged into a reactor equipped with a stirrer, a gas inlet and a gas outlet. Nitrogen gas and/or oxygen gas or an oxygen-containing gas is fed into a reactor to replace the atmosphere within the reactor or to increase the pressure within the reactor, and the reaction system is heated to a predetermined temperature. Stirring or feeding of oxygen or oxygen-containing gas is not always necessary during the temperature elevation period. The absorption of oxygen is initiated usually at a temperature of about 100° C. although the temperature is variable depending on the amount or composition of the catalyst to be used. After initiation of oxygen absorption, oxygen or oxygen-containing gas is introduced into the reactor at a predetermined temperature, whereupon the reaction is conducted while maintaining the above-specified total reaction pressure and partial pressure of oxygen. The discharged gas is cooled and the condensate is returned to the reactor. The reaction is usually conducted for about 0.1 to about 10 hours, although the reaction time is variable depending on the amount and composition of the catalyst used, concentration of the starting material, etc.

After completing the reaction, the reactor is cooled and the reaction mixture is withdrawn. The reaction mixture as it is or after evaporation in part of the solvent is cooled to thereby crystallize the desired diphenyl sulfonetetracarboxylic acid, or alternatively the reaction mixture is evaporated to dryness and the residue is subjected to recrystallization.

Usable as the solvent in the recrystallization is water or a mixture of water and an organic solvent. The organic solvent in the mixture can be any of organic solvents missible with water. Examples of useful organic solvents are formic acid, acetic acid, propionic acid, butyric acid, valeric acid, caproic acid, enanthic acid, caprylic acid and like aliphatic carboxylic acids, methanol, ethanol, propanol, butanol, isopropanol and like aliphatic alcohols, ethyl acetate and like esters, acetone, methyl ethyl ketone, cyclohexanone and like ketones, ethyl ether, dioxane and like ethers, acetonitrile, methylene chloride, chloroform, etc.

It is possible in the invention to use other types of reactors than the above type equipped with a stirrer, such as a bubble-tower type reactor.

The reaction methods are not limited only to batchwise methods but include continuous and semicontinuous methods. For example, the starting material, catalyst and solvent are continuously fed into a reactor and then the reaction is conducted while feeding oxygen or oxygen-containing gas into the reactor and continuously withdrawing the reaction product. According to another embodiment, a reactor is charged with the catalyst and the solvent and then with the starting material alone or together with the solvent. After a certain period of reaction, the feeding of the starting material (and the solvent) is discontinued, followed by reaction until completion.

EXAMPLES

The invention will be described below in greater detail with reference to the following Examples and

COMPARISON EXAMPLES

The purity and yield of the desired reaction products obtained in the Examples and Comparison Examples were determined by high performance liquid chromatography (HPLC) after the metal salt used as the catalyst component in the crude product was decomposed with a mineral acid. Thus, for examle, 100 ml of 1N nitric acid was mixed with 1 g of the crude reaction product and the mixture was refluxed for 1 hour, and 1 ml portion of the resulting mixture was diluted with a HPLC mobile phase to 25 ml, followed by the HPLC analysis.

The color of the desired product (APHA, American Public Health Association method, also called Hazen number) was determined using the product obtained by removing the cobalt and manganese components from a 20% aqueous solution of the crude reaction product with use of a cation exchange resin (tradename "Diaion PK-228," product of Mitsubishi Kasei K.K.). A preferred APHA value is 150 or less.

EXAMPLE 1

A 1.5 l-vol. titanium autoclave equipped with a gas inlet, a gas outlet with a reflux condenser, a thermometer and an electromagnetic stirrer was charged with 150 g of 3,3',4,4'-tetramethyldiphenyl sulfone (hereinafter referred to as "TMS"), 6.70 g of cobalt bromide [CoBr$_2$.6H$_2$O], and 0.55 g of manganese acetate [Mn(OCOCH$_3$)$_2$.4H$_2$O] and 850 g of acetic acid. The Mn/Co ratio of the catalyst was 0.1. Nitrogen gas was introduced to increase the pressure to 18 kg/cm$^2$G, and the mixture was heated with stirring. Air was introduced into the liquid phase of the reaction system when the temperature of the reaction system reached 160° C. Thereafter the reaction temperature was maintained at about 170° to 180° C. The vaporized acetic acid was condensed and recycled to the reaction system, and the amount of air to be fed was adjusted so as to maintain the total reaction pressure of 20 kg/cm$^2$G and so as to maintain the partial pressure of oxygen at 1.1 atm. or lower (sometimes the partial pressure of oxygen became zero due to full consumption of the oxygen fed). After about 2 hours of reaction, the absorption of oxygen was scarcely recognized, whereupon the feed of air was discontinued. The reaction product in the reactor was withdrawn after the reactor was cooled. The solvent was distilled off under reduced pressure, giving 220 g of a crude oxidation product. The obtained crude reaction product had a neutralization value of 567, and the desired 3,3',4,4'-diphenyl sulfonetetracarboxylic acid (hereinafter referred to as "DSTC") was produced with a purity of 96.8% in a yield of 99.0%. The product had a color (APHA) of 50.

EXAMPLE 2 to 5

DSTC was prepared under the same conditions as in Example 1 except that the Mc/Co ratio was changed by varying the amount of manganese acetate to be fed. Table 1 below shows the results.

COMPARISON EXAMPLE 1

DSTC was prepared in the same manner as in Example 1 with the exception of using 0.0055 g of manganese acetate (Mn/Co=0.001). Table 1 below shows the result.

COMPARISON EXAMPLE 2

DSTC was prepared in the same manner as in Example 1 with the exception of using 0.0270 g of manganese acetate (Mn/Co=0.005). Table 1 shows the result.

COMPARISON EXAMPLE 3

DSTC was prepared in the same manner as in Example 1 with the exception of using 3.7700 g of manganese acetate (Mn/Co=0.70). The result is shown in Table 1.

COMPARISON EXAMPLE 4

DSTC was prepared in the same manner as in Example 1 with the exception of using manganese acetate in an amount of 5.0000 g (Mn/Co=0.93) according to a conventional Mn/Co ratio. The result is shown in Table 1.

TABLE 1

| | Amount of manganese acetate (g) | Mn/Co (wt. ratio) | DSTC Purity (%) | Yield (%) | Color (APHA) |
|---|---|---|---|---|---|
| Example | | | | | |
| 2 | 0.0550 | 0.01 | 96.5 | 97.8 | 40 |
| 3 | 0.2700 | 0.05 | 96.7 | 98.3 | 50 |
| 4 | 1.5000 | 0.28 | 96.5 | 98.8 | 80 |
| 5 | 2.6900 | 0.50 | 95.5 | 97.3 | 120 |
| Comp. Ex. | | | | | |
| 1 | 0.0055 | 0.001 | 84.6 | 87.1 | 40 |
| 2 | 0.0270 | 0.005 | 87.7 | 91.2 | 40 |
| 3 | 3.7700 | 0.70 | 94.6 | 95.4 | 300 |
| 4 | 5.0000 | 0.93 | 89.9 | 93.7 | 350 |

Table 1 shows that a high-purity diphenyl sulfonetetracarboxylic acid of proper color can be prepared in a high yield when tetramethyldiphenyl sulfone is oxidized with oxygen or an oxygen-containing gas in the presence of a cobalt-manganese-bromine compound combination as a catalyst having the composition as defined in the present invention.

EXAMPLE 1

The same reactor as used in Example 1 was charged with 150 g of TMS, 850 g of acetic acid and as a catalyst (Mn/Co=0.10), 5.10 g of Co(OAc)$_2$.4H$_2$O, 0.55 g of Mn(OAc)$_2$.4H$_2$O and 13.0 g of hydrobromic acid (HBr, 47%). Oxidation reaction was conducted in the reactor under the conditions of a reaction temperature of 180° to 190° C. and a total pressure of 15 kg/cm$^2$G (partial pressure of oxygen being maintained at 0.8 atm. or lower), giving DSTC with a purity of 96.4% in a yield of 98.9%.

EXAMPLE 7

The same procedure as in Example 1 was conducted with the exception of using 2,3,3',4'-tetramethyldiphenyl sulfone as tetramethyldiphenyl sulfone, whereby the corresponding tetracarboxylic acid was produced with a purity of 96.4% in a yield of 98.7%. The product had a color (APHA) of 50.

EXAMPLE 8

The same procedure as in Example 1 was conducted with the exception of using 2,2',3,3'-tetramethyldiphenyl sulfone as tetramethyldiphenyl sulfone, whereby the corresponding tetracarboxylic acid was produced with a purity of 96.5% in a yield of 98.1%. The product had a color (APHA) of 50.

EXAMPLE 9

The same procedure as in Example 1 was conducted with the exception of using a 9:1 mixture (weight ratio) of TMS and 2,3,3',4'-tetramethyldiphenyl sulfone in place of TMS, whereby the corresponding tetracarboxylic acid was produced with a purity (i.e., purity of tetracarboxylic acids including all the isomers) of 96.1% in a yield of 98.5%. The product had a color (APHA) of 50.

EXAMPLE 10

DSTC was prepared in the same manner as in Example 6 with the exception of using, as the catalyst (Mn/Co=0.28), 20.0 g of cobalt naphthenate (Co content=6%), 1.50 g of Mn(OAc)$_2$.4H$_2$O and 8.23 g of sodium bromide.

Thus DSTC was prepared in a yield of 98.5% and the thus-obtained DSTC had a purity of 96.8% and a color (APHA) of 50.

EXAMPLE 11

DSTC was prepared in the same manner as in Example 6 with the exception of using, as the catalyst (Mn/Co=0.10), 5.10 g of Co(OAc)$_2$.4H$_2$O, 1.21 g of manganese naphthenate (Mn content=10%) and 5.60 g of tetrabromoethane.

Thus DSTC was prepared in a yield of 97.5% and the thus-obtained DSTC had a purity of 96.3% and a color (APHA) of 50.

We claim:

1. A process for preparing a diphenyl sulfonetetracarboxylic acid, the process comprising oxidizing a tetramethyldiphenyl sulfone with oxygen or an oxygen-containing gas in an aliphatic monocarboxylic acid having 2 to 10 carbon atoms in the presence of a catalyst consisting essentially of a cobalt component, a manganese component and a bromine compound wherein the weight ratio of manganese metal to cobalt metal is in the range of approximately 0.01 to 0.5.

2. A process according to claim 1 wherein the cobalt component is metal cobalt, cobalt oxide, cobalt hydroxide, cobalt salt or cobalt complex.

3. A process according to claim 1 wherein the manganese component is metal manganese, manganese oxide, manganese hydroxide, manganese salt or manganese complex.

4. A process according to claim 1 wherein the bromine compound is bromine molecule, hydrogen bromide, bromic acid, hypobromous acid, bromide, bromate, hypobromite or an organic bromine compound.

5. A process according to claim 1 wherein the bromine compound is at least one member selected from the group consisting of hydrogen bromide, ammonium bromide, alkali metal bromide, alkaline earth metal bromide, cobalt bromide, manganese bromide, cerium bromide, tetrabromoethane and tribromoethane.

6. A process according to claim 1 wherein the bromine compound is at least one member selected from the group consisting of hydrogen bromide, ammonium bromide, sodium bromide, potassium bromide, cobalt bromide, manganese bromide, cerium bromide, tetrabromoethane and tribromoethane.

7. A process according to claim 1 wherein the catalyst is one selected from the group consisting of cobalt bromide-manganese bromide; cobalt bromide-manganese acetate; cobalt acetate-manganese acetate-hydrogen bromide; cobalt acetate-manganese acetate-ammonium bromide; cobalt bromide-manganese naphthenate; cobalt naphthenate-manganese naphthenate-hydrogen bromide; cobalt acetate-manganese naphthenate-tetrabromoethane; cobalt acetate-manganese acetate-sodium bromide; and cobalt acetate-manganese bromide-cerium bromide.

8. A process according to claim 1 wherein the cobalt component is used in an amount of about 0.01 to about 20 g, calculated as cobalt metal, per liter of the combined amount of the components present in the liquid phase of the reaction system.

9. A process according to claim 1 wherein the cobalt component is used in an amount of about 0.01 to about 10 g, calculated as cobalt metal, per liter of the combined amount of the components present in the liquid phase of the reaction system.

10. A process according to claim 1 wherein the weight ratio of the manganese metal to the cobalt metal is about 0.01 to about 0.3.

11. A process according to claim 1 wherein the bromine compound is used in an amount of about 0.05 to about 100 g, calculated as bromine atom, per liter of the combined amount of the components present in the liquid phase of the reaction system.

12. A process according to claim 1 wherein the bromine compound is used in an amount of about 0.05 to about 50 g, calculated as bromine atom, per liter of the combined amount of the components presenr in the liquid phase of the reaction system.

13. A process according to claim 1 wherein the tetramethyldiphenyl sulfone is used in an amount of about 35 to about 950 g per liter of the combined amount of the components present in the liquid phase of the reaction system.

14. A process according to claim 1 wherein the tetramethyldiphenyl sulfone is used in an amount of about 50 to about 500 g per liter of the combined amount of the components present in the liquid phase of the reaction system.

15. A process according to claim 1 wherein the aliphatic carboxylic acid is a saturated lower aliphatic carboxylic acid.

16. A process according to claim 1 wherein the aliphatic carboxylic acid is acetic acid.

17. A process according to claim 1 wherein the aliphatic carboxylic acid is used in an amount of about 50 to about 920 g per liter of the combined amount of the components present in the liquid phase or the reaction system.

18. A process according to claim 1 wherein the aliphatic carboxylic acid is used in an amount of about 475 to about 910 g per liter of the combined amount of the components present in the liquid phase of the reaction system.

19. A process according to claim 1 wherein the oxidation reaction is conducted at a temperature of about 100° to about 250° C.

20. A process according to claim 1 wherein the the oxidation reaction is conducted at a temperature of about 150° to about 210° C.

21. A process according to claim 1 wherein the oxidation reaction is conducted at a total pressure of about 1 to about 50 kg/cm$^2$G and a partial pressure of oxygen of about 8.0 kg/cm$^2$ or lower.

22. A process according to claim 1 wherein the oxidation reaction is conducted at a total pressure of about 3 to about 30 kg/cm$^2$G and a partial pressure of oxygen of about 6.0 kg/cm$^2$ or lower.

* * * * *